US009592464B2

(12) United States Patent
Prax

(10) Patent No.: US 9,592,464 B2
(45) Date of Patent: Mar. 14, 2017

(54) HVAC FILTRATION SYSTEM

(71) Applicant: Xavier Rex Prax, Willoughby Hills, OH (US)

(72) Inventor: Xavier Rex Prax, Willoughby Hills, OH (US)

( * ) Notice: Subject to any disclaimer, the term of this patent is extended or adjusted under 35 U.S.C. 154(b) by 230 days.

(21) Appl. No.: 14/097,142

(22) Filed: Dec. 4, 2013

(65) Prior Publication Data

US 2014/0150658 A1   Jun. 5, 2014

Related U.S. Application Data

(60) Provisional application No. 61/733,084, filed on Dec. 4, 2012.

(51) Int. Cl.
*B01D 46/00* (2006.01)
*B01D 46/10* (2006.01)

(52) U.S. Cl.
CPC ..... *B01D 46/0005* (2013.01); *B01D 46/0002* (2013.01); *B01D 46/0032* (2013.01); *B01D 46/10* (2013.01); *B01D 2265/023* (2013.01)

(58) Field of Classification Search
CPC  B01D 46/0002; B01D 46/0005; B01D 46/10; B01D 46/0032; B01D 2265/023
See application file for complete search history.

(56) References Cited

U.S. PATENT DOCUMENTS

| | | | |
|---|---|---|---|
| 5,720,660 A * | 2/1998 | Benedetto et al. | 454/284 |
| 6,793,715 B1 * | 9/2004 | Sandberg | 95/273 |
| 7,811,346 B1 * | 10/2010 | Henson | 55/385.1 |
| 2010/0005624 A1 * | 1/2010 | Swearingen | F16G 11/00 16/110.1 |
| 2010/0071324 A1 * | 3/2010 | Alexander et al. | 55/492 |
| 2010/0126129 A1 * | 5/2010 | Kim et al. | 55/494 |
| 2011/0030557 A1 * | 2/2011 | Brownstein et al. | 95/273 |
| 2013/0212990 A1 * | 8/2013 | Albert | 55/373 |

* cited by examiner

*Primary Examiner* — Robert Clemente
(74) *Attorney, Agent, or Firm* — Dodd Call Black, PLLC; Dustin L. Call

(57) ABSTRACT

This invention pertains to interchangeable, disposable, air filtration pads, which work in conjunction with its double-sided flexible magnetic gaskets and mats. This system works both for return and supply side of the HVAC system. This multi-adaptable double-sided magnetic mat system is easily attachable and removable and compatible to current factory vent plates, and HVAC systems.

19 Claims, 8 Drawing Sheets

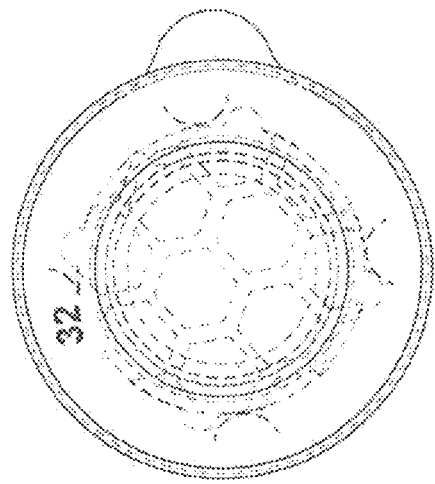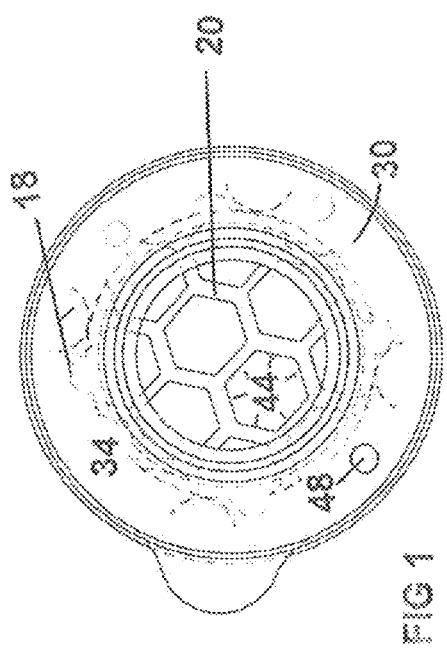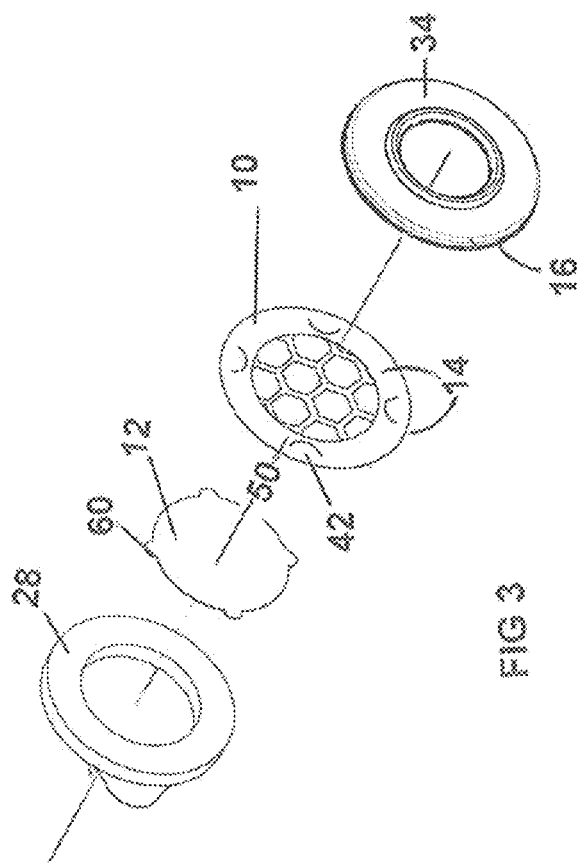

HVAC FILTRATION SYSTEM

PRIORITY

This document claims priority to and incorporates by reference in its entirety U.S. provisional application 61/733,084 filed by Xavier Rex Prax on 4 Dec. 2012.

BACKGROUND OF THE INVENTION

1. Field of the Invention

The present invention relates to heating, ventilation and air conditioning systems, and more particularly, to air quality filtration systems therefor.

2. Problems Solved by Invention
Interchangeable Filter
   A. Attracts and captures microscopic particles like smoke and smog and large allergens like mold spores and pollen from the air passing through the filter.
   B. Scented infused filters, able to disperse various or independent scents room to room. Example girls room something flowery, boys room a clean scent, while a Holiday scent in the living room.

Current products do not offer an external easy on easy off air duct filter system. The current air filter system located on the air intake or under the duct registers faceplate.

3. Benefits to Users of Invention

Current HVAC systems have the air filters at the intake portion of the furnace and/or the air-conditioning handler.

This system allows for dust and dirt, which may be in the duct system to be filtered at every air duct exit vent plate fascia.

The consumer can easily change out the economical filters often to maintain the highest level of filtration and avoidance of reintroduction of previously captured contagions.

4. Reference Numeral Summary
10—Grille mat
12—Filter pads
12a.—Filter screen pads
14—Double sided flexible magnetic vinyl
16—Single sided flexible magnetic vinyl
18—Die Cut Magnetic self-clip griping system,
20—"The Grille" die cut out pattern
24—Contact margin direct surface point of contact
26—Faceplate control kiss stamp, for optional leave in or removable cut out
28—Gasket mat
30—Gasket topside
32—Gasket bottom side
34—Frame mat
36—Lidding flange sleeve
38—Vent blocker insert panel
40—Existing Affixed duct vent fascia cover/Hot or cold "air exit"
42—Crescent die cut tab cinching
44—Multi directional/honeycomb pattern
48—Counter sink magnets
50—"Grille mat system" components
60—Removable replaceable filter pad tabs
62—Air return or air point of entry
64—Air duct
66—HVAC existing disposable slide track filter

SUMMARY OF THE INVENTION

This invention pertains to interchangeable, disposable, air filtration pads, which work in conjunction with its double-sided flexible magnetic mats. This system works both for air-intake and air output side of the HVAC (heating ventilation and air conditioning) system. This multi-adaptable double-sided magnetic mat system is easily attachable and removable and compatible to current factory vent plates, and HVAC systems.

When referring to air vents, this may also refer to the air-ducts (out-put) or point of exit. These outlets are typically located, on the ceilings and floors of homes, automobiles and airplanes. When referring to HVAC and or AC handlers, this refers to the systems in-take or air return. points.

The double magnet or gasket adhesive system attaches over the top off these existing air duct registers vent, and faceplates. The double side magnetic flexible vinyl configuration allows for the ducts exited Air output, to be filtered at the vent fascia.

Any of the magnets and magnetic features shown herein could be single and/or double sided magnets if needed to adhere the mating surfaces together with more or less strength. The specific application could dictate the magnet orientation and strength.

Now just flip the double-sided magnetic "Mat Grille" component, and the same air filter system becomes HVAC handler the vent air intake filter system (FIG. 9).

The purpose of this invention is to provide an additional and affordable forced air filter system. These affordable filters pads works in conjunction with existing HVAC systems filter.

These non-woven air filter pads are positioned under a die cut magnetic vinyl venire and positioned and magnetically held for a metal surface. And in the case of non-metal surface the bottom of the gasket is secured with an adhesive, than the components are placed over the HVAC forced air exit register plate. These filter pads are held into position behind a die cut crescent-moon magnetic lift and stick tabs.

These pads will attract and accumulate additional airborne particles, not captured HVAC current intake handler filter.

Current HVAC systems (FIG. 9) typically only have one filter at the intake portion of the furnace and/or the HVAC handler. This current flawed system allows for dust and dirt, which may be in the duct system to be filtered at every air duct exit vent plate fascia. Most commercially purchased fiberglass filters are only 7% efficient in stopping dirt, dust, pollen, etc. from passing through it. (Source, ASHRAE)

The consumer can easily change out the economical filters often to keep a much higher standard of air quality.

BRIEF DESCRIPTION OF THE DRAWINGS

With the above and other related objects in view, the invention consists in the details of construction and combination of parts as will be more fully understood from the following description, when read in conjunction with the accompanying drawings in which:
FIG. 1 Front elevation view.
FIG. 2 Back elevation view.
FIG. 3 Exploded perspective view.

DETAILED DESCRIPTION OF THE PREFERRED EMBODIMENT

Figure 4:
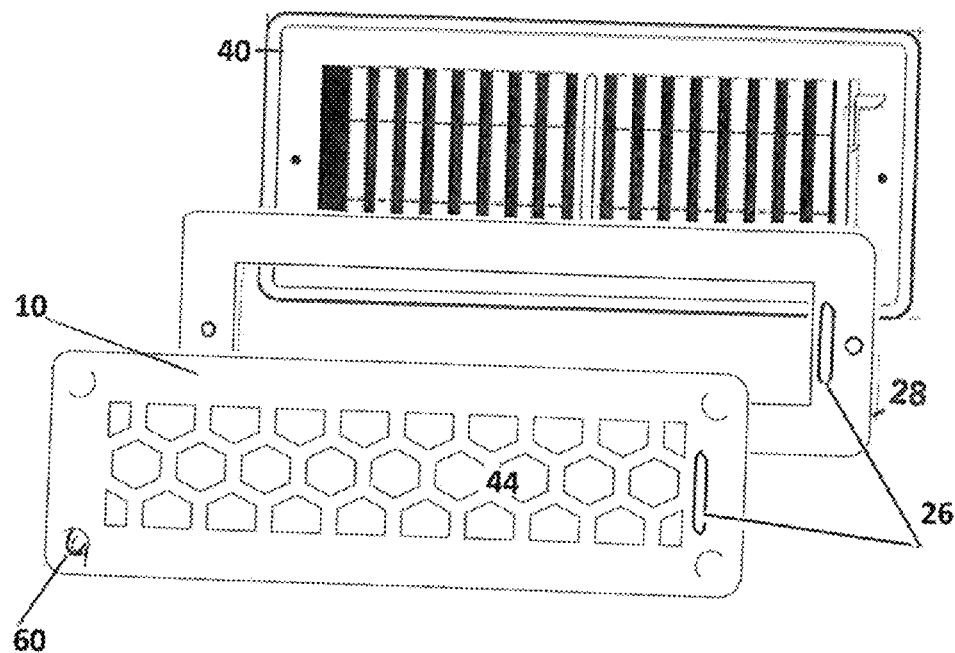
FIG. 4 Front elevation view with filter inserted.
Figure 5:
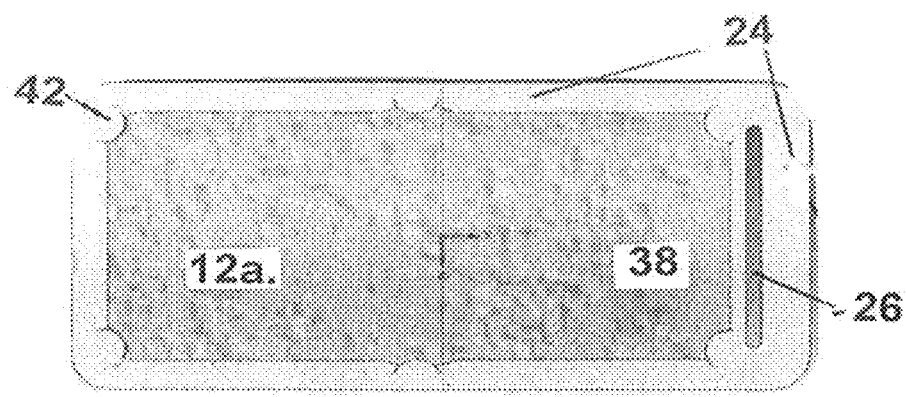
FIG. 5 Back elevation view with filter inserted.
Figure 7:
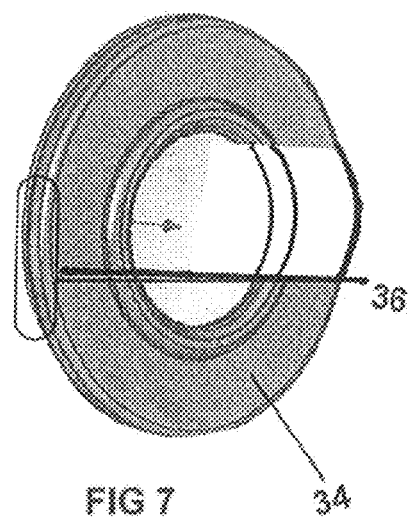
FIG. 7 Perspective view of flange sleeve.
Figure 6:
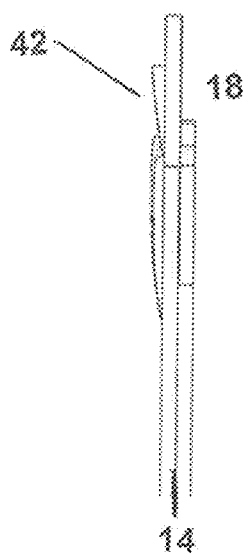
FIG. 6 Side elevation view of filter pad magnetic clip system.
Figure 8:
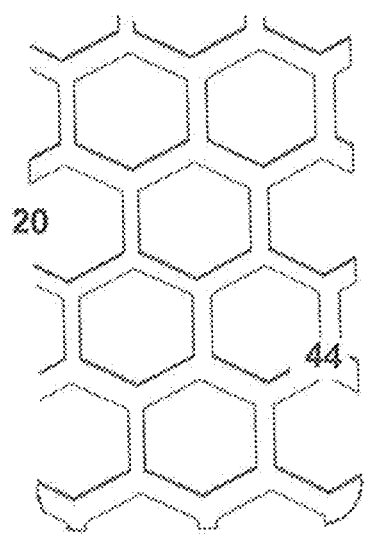
FIG. 8 Elevation view of an example of a cut grille pattern.

This convenient and multi-functional and versatile vent filter system is non-invasive, and does not require assembly. This unique system works in conjunction with most wall, ceiling, and dashboard fuchsia vent duct covers. This versatile multi-functional vent system will adhere to metal or non-metal surfaces and will work with a variety of stock factory air duct (64) systems vents (40 & 62). Since the filter overlay frame matting (10) in its assembled entirety is used as an after-market item and this control kiss stamped (26) works in conjunction with the existing vent controls.

The filter overlay framing mat (10) works in conjunction with the frameless filter pad inserts (12), and, the affixed vents outlet (40 & 62), opening in current, metal, or non-metal plate factory or stock air vent (40 & 62).

So as not to interfere with the directional, on/off or closed vent positions. The kiss stamped panel may remain intact in the filter overlay frame matting (10) or it may be completely removable/cut out. The matting frame (10) is a double side magnetic flexible vinyl (14), which allows for the mat frame (10) to adhere its self to a metal vent (40) on the backside.

The double side magnetic flexible vinyl (14) also allows for the mat frame to adhere to the bottom magnetic laminated layer of "over frame panel" (38). The "over frame panel" (38) assists in securing all of the filter pad (12) tabs (60) by applying additional magnetic pressure to the clip grip system (18) and the "Crescent die cut tab cinching" (42) The top magnetic layer of double side magnetic flexible vinyl (14) also supports the adhesion of micro magnets (48) to vents (40 & 62) which may have been painted or may have a mixed base metal, this creates a weaker vinyl magnetic (14) attraction and weak adhesion. The single and/or double side magnetic flexible vinyl (14) also provides a top facing magnetic field to adhere the extra pull micro magnets (48) positioning.

Also once these extra strong pull Micro-magnets (48) are counter sunk to the gasket (28), are less likely to become misplaced or lost. These Micro-Magnets (48) support the glue less, screw less, or snap together, sequencing assembly of related components.

The air filter pad (12) is a non-ridged single or multi-layer structure. The filter pad (12) is constructed from a static charged, synthetic fibrous non-woven like "Swifter" floor dusting pads. These "air dusting filter pads (12)" help to collect and trap air borne dust, hair dirt and mold and pollen spores.

When the Filter pads become dirty they are easily changeable or exchangeable, for a new or clean and or washed filter pad on a regular basis. In addition this filter pad (12) and Frame mat (10) create a system for interchangeable applications, tasks and or performance.

Applications for specialty pads may include scent infused filter pads, able to disperse various or independent scents room to room. A room to room application "Girls room something flowery", "The master bedroom a clean scent", while a Holiday scent in the living room.

Performance pad inserts, which would attract and capture microscopic particles like smoke and smog and large allergens like mold spores and pollen from the air passing through the filter. Yet another function is to block cold air in winter months with a vent air-blocking insert (42). Yet another specialty pad is an eco-friendly machine washable, re-usable dust filter pad (12).

The filters could also use an activated carbon element to further capture particulate matter, odors, chemical vapors (such as organic compounds) and other matter carried by or dissolved in the air passing through the system.

The filter pads (12) have protruding die cut tabs (60). These protruding tabs assist in the initial filer pads pull through (22b). The protruding tabs allow for the filter pads proper alignment/positioning (22c). The protruding tabs than positioned under the die cut self-clip Griping mechanism (18). This self-clip griping mechanism works in conjunction with the crescent cinching (44) self-tightening, creating a narrowing point of entry, and gradually tightens until the crescent cut out.

Yet another function for the Clip grip (18) and self-tightening crescent cinching (44) is that they accommodate not only a solo pad (12) but also multiple pads (12.) Example one dust control screen plus one air-fleshing pad and serves to secure the filter pad (12) to the (10) s filter overlay frame matt (34)—Attachable frame over lay flange (34) for a metal adhesion this filters frame mat would be laminated. with (34a) magnetic sheeting and non-metal and or (10) the disposable units a (34b) Re-applicable low tack adhesive (water based or others) (34c) crack and peel liner (sometimes called a pressure sensitive adhesive with removable backing).

The single piece filter overlay frame mat vent plate cover (10) has die cut lift tabs are incorporated to position and secure the filter pad in (10) the frames (36) adhesion margin. Once the non-woven filter pad (12) with (12a) is positioned and placed underneath the vent plate mats (10) Grille (20). A positive negative space is created via the die cut mat grille (20). The die cut surface creates a serves in the prevention of the filter pads from bunching and bulging. Thereby assisting in the reduction of dust and dirt or mold from escaping around the fibrous filter pads (12).

The grille mat (20) prevention of filter blowing out and/or away from the duct vent plate and the grille (20) and the existing affixed vent outlet (40). This positive and negative die cut space also creates non-restrictive in-take airflow of the HVAC furnace or AC handler. This positive and negative die cut space also creates a non-restrictive and duct vents (40 & 62) in or out-put air flow.

In the case of a metal affixed. vent outlet (40) and a magnetic vinyl is used on the matt (10) and the grille (20) this creates a crosshatch multi directional pattern. (44). This then creates positive negative space with the multi directional pieces removed from (10) solid piece of laminated vinyl materials die cut multi directional pattern grille (20). The positive/negative die cut space pattern applies a constant pressure to the top of (12) non woven filter pad.

(20b) Prevent nonwoven air filters from bulging and thus allowing dust and dirt or mold to escape around the fibrous filter. (20c) Prevention of filter blowing out and/or away, or bunching between the duct vent plate and the vinyl magnetic materials. Combined with the magnetic (16) a. pressure of (20) the positive/negative die cut open and closed space pattern cut out or negative space allows for the forced air to exit from the duct. The positive/negative die cut open and closed space pattern magnetic material, allows for the non-woven materials to de-compress under the magnetic adhesion pressure and expand up through these die cut opening.

The filtering media may have an electrostatic charge to aid the filter media in attracting and collecting from the air many airborne particulates such as dust, odor causing particles, dander and many other floating matter that could otherwise potentially pass through the filter and be readmitted to the breathing air.

This repetitive positive/negative die cut open space pattern allows a north/positive and south/negative polar opposite magnetic current electromagnetic blanket coverage. Yet another of grille (20) benefit, is that the die cut crosshatch positive negative space supports and works with magnetic characteristics. Magnetic north is negative and magnetic south is positive. The resulting magnetic field lines go from north to south.

A. Magnetic lines of force start from the North Pole and end at the South Pole, B. They are continuous through the body of magnet C. Magnetic lines of force can pass through iron more easily than air. D. They tend to contract longitudinally. E. They tend to expand laterally. Prevents, the use of any adhesive materials to be used on (12) the non-woven filter. Continues pulling pressure point (18-18a) Die cut self-clip griping system. (18a) Magnetic (18h) Crack and peel liner with adhesive to secure the pad, these filter pads (12) used may be disposable or washable.

Yet another of grilles (20) benefit is that the die cut crosshatch positive negative space supports and works with the magnetic characteristics to help adhere the grille mat (20) to the metal vents face plate (40) 10, 20 and 36 Framing laminate underside will be (16a) Magnetic sheeting for metal vents and (16b) could be used for any non-metal adhesion and other applications, but not limited to re-applicable low tack adhesive (water base, or others) (16c) crack and peel liner.

The (10) filter overlay frames topside material (14) may be constructed from a primary and or secondary materials (14a) PVC vinyl (14b) Plastic (14c) Paper Cardboard, could be used in a economical disposable frame filer unit used in various environmental conscious locations like hospitals, and other health care institutions, where sanitation and hygiene is of top propriety, 100% disposable non-re-useable materials could be applied. This material would include, but not limited to, (14a) die cut vinyl, (14c) paper, and frame. Liner (16c) backed water-based (16c) adhesive. These adhesive characteristics include, not damaging the applied surfaces finish, and also offer the ability to be repositioned.

The magnetic gasket mat (28) would serve as an elevated surface to mount the mat overlay (10) and the filter pads (12) this is to avoid. any existing protruding venting (40) controls, on/off, or directional knobs etc.) These conditions exist in many public settings such as jet airliners, auto dashboards, and office workspaces. There may, or may not be metal for the magnetic to attach. If metal is available the elevated would have a magnetic ring seals adhered on both ends of gasket (28). One top side with (north pole) (30 a) and (south pole) (32 a) adhered the other bottom side. Original factory constructed surface with non-magnet vents (40) like a jetliner, an elevated magnetic gasket would have a magnetic ring seals (north pole) adhered on one end, to adhere to mats (10) bottom side (16a) (south pole) and an adhesive seal ring (32b) and crack and peek liner (32c) on the other end of gasket (28).

The gasket (28) (optionally magnetic or adhesive, depending on the application) also may act as female mate to overlay frame cover overlays (34) optional male lidding sleeve flange (36) this interacts to secure the grille framed mat (10) Filter pad (12) and the optional filter pad tabs (12a). Many vents have painted or a mixed base metal, this creates a weaker vinyl magnetic (14) attraction and weak adhesion.

Another feature the magnetic gasket would have is counter sunk holes (48) keeping a flush adhesion surface, and strong micro magnets (46) would be inserted in the gasket (28). This will greatly increase magnetic pull strength and strong micro magnets (46) would be inserted in the gasket (28).

This greatly increases the magnetic fields pull strength.

The magnetic gasket (28) also allows for the entire "Air filter system" to be adhered to any non-metal surfaces like plastic or drywall. For the disposable units gasket (28) application the gasket topside (30) re-applicable tack adhesive (30b) along with a removable crack and peel liner (30c) and gaskets bottom side (32) re-applicable low tack adhesive (32b) (water base or others) This combination of base mounted gasket (28) and top fascia cover (38) along with a removable crack and peel adhesive (32b) and crack and peel liner (32c).

The frame overlay (34) may or may not require lidding sleeve flange (46) and may come in direct contact with the frames (10) margin of direct contact (24). This fascia cover (34) covers and hides the filer tab pull (60) through. This fascia cover (34) is printable, for all forms of graphics, including novelty applications holograms, glow in the dark, printed patterns, cartoon characters etc.

(24) Frame matting direct surface point of contact (24a) for an un-obstructed metal surface adhesion magnetic (24b) Un-obstructed non-metal surface adhesion and (24c) Disposable low tack, reuseable, non-invasive re-adhesion.

(36)—Attachable Frame Over Lay Flange (36a) Magnetic sheeting (36b) Re-applicable low tack adhesive that can be reused water based or other (36c) Crack and peel liner (36d) Lidding non-adhesive pressure, male/female lidding flange.

Figure 9:
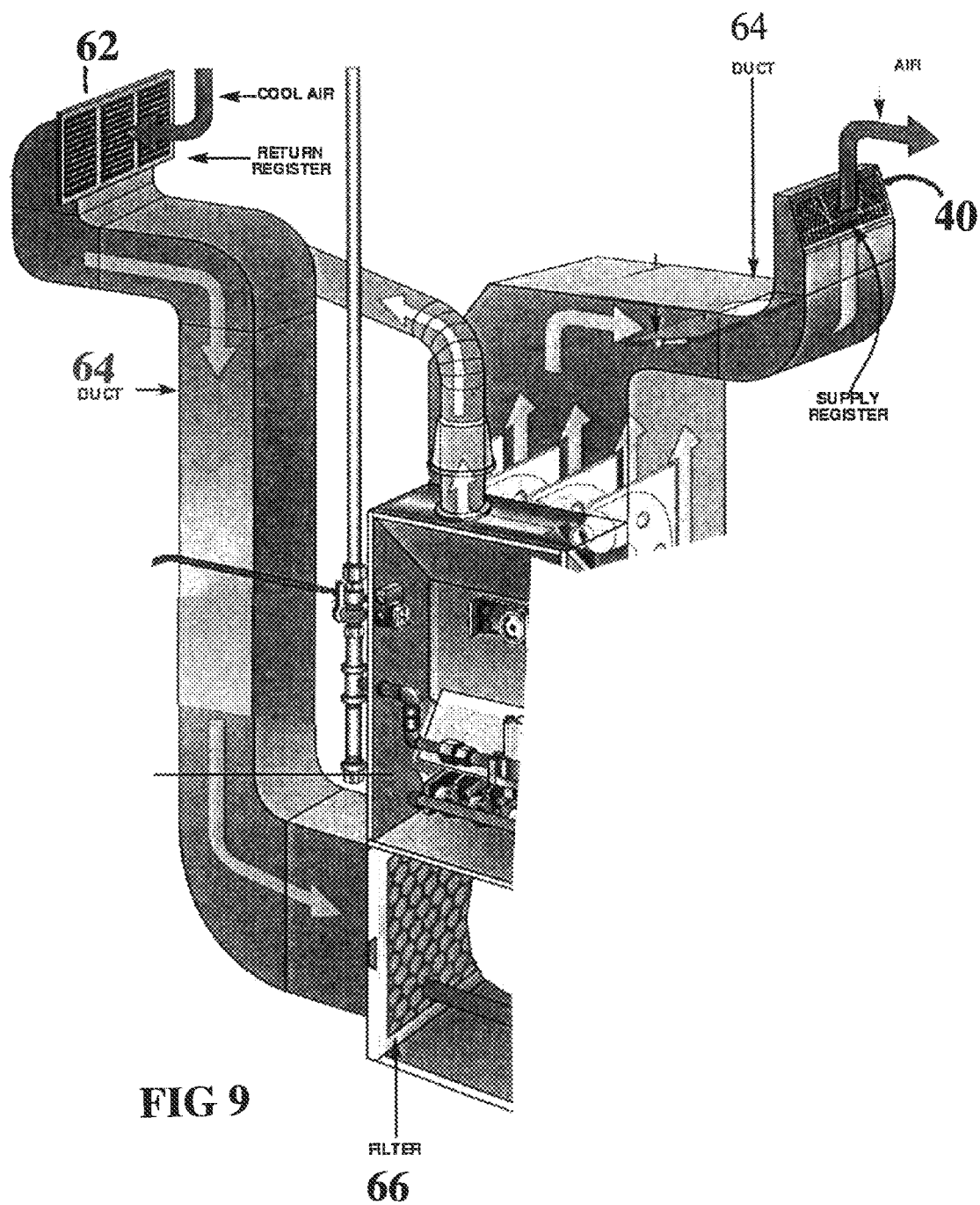
FIG. 9 Conventional air-conditioning system diagram.

FIG. 9 Configuration for air-intake/return use.

The single and/or double sided magnetic flexible vinyl (14) also allows for the air output (push) configuration—Frame mat overlay (34) 2.—Grille mat (10) 3. Filter pad 4.—Gasket (28). Simply flip the mat grille (10) and the filter pads (12) the adhere to the bottom magnetic laminated layer of "over frame mat (34)" And now with these simple component directional change, the vent air flow output filter system, now becomes a HVAC handler secondary intake filter. Current HVAC furnace, and air conditioner unit handler's replacement filters (66) typically slide in a three-sided metal track. Also these replacement filters do not have any gasket adhered which becomes a key culprit of inefficient air filtration. This current antiquated. filter system has only a 7% effectiveness in stopping dust, dirt, pollen, etc. (Source, ASHRAE).

This "Air Return" (62) configuration will increase the life of the HVAC slide track filter. This "Air Return" (62) configuration reduces the intake of dirt, pollen, and pet dander and thus extends the life of furnace. This "Air Return" (62) configuration reduces the intake of dirt, pollen, and pet dander and thus requires less duct cleaning and maintenance. This "Air Return" (62) configuration reduces the intake of dirt, pollen, and pet dander and thus improves overall air quality.

Therefore when using the "Grille Mat" (10) filter pads (10) Gasket (28) and other components (50) will increase the efficiency of the current furnaces existing filter (66). Furthermore the gasket will reduce dust, dirt, and hair from being inhaled through the furnace, and ducts. Furthermore, using the grille mat system (50) will extend the life of the HVAC furnace, and Air conditioner units, replacement filter. Furthermore the grille mat system (50) will improve the overall interior air quality. Furthermore the grille mat system

(50) will educe the accumulation of dust and dirt on the furnace coils, thus reducing maintained costs of upkeep, and service calls.

Furthermore the grille mat system (50) will keep duct systems (64) cleaner. Furthermore grille mat system (50) will reduce cost by reducing duct systems (64) maintenance and cleaning service.

This after market air filter system is accessible and user friendly. With the magnetic laminated metal vent face plate system is applicable, magnetic self-adhering properties are applied to an optional "die cut" tab where absolutely no adhesive is required to position and hold the disposable, or machine washable filters. Also in the case of a non-magnet to metal contact adhesion compatibility such as ceiling, car vinyl dashboards, aircraft overhead vents, flooring, and any forced air duct exits, there may be no metal for the magnetic to attach, an adhesive, in those scenarios, a backed magnet flexible gasket may be incorporated. (This gasket (28) may also serve as an elevated surface mount to avoid any existing protruding venting controls, on/off, or directional knobs etc.)

In public settings like airline jets, office workspaces, a double-sided/+/−North and South Pole magnet application would apply. This would allow for a quick filter change out, while the original magnetic filters base would stay fixed adhered to the original factory constructed surface. In addition this removable top fascia is also printable for branding, graphics, or advertisements. In addition, this benefits including interchangeable, disposable filters, such as a variety of scents.

This unique aftermarket air filter system is accessible and user friendly. The filter its self requires no adhesives. The magnetic framing and gasket assembly (50) offers the self-grasping and/or tab system. In the case if there is a non-metal or non-magnetic adherence surface an adhesive with a crack and peel liner would be applied to the back frame system (50). This would be applied to secure the filter pads (12). By using the magnetic clinging properties, this original filter tab latch system has have been developed. The self-adhering magnetic tab is used in such a way; where absolute no adhesive is required on the non-woven changeable disposable or machine washable filters. Also in the case of a non-magnet to metal contact adhesion compatibility such as ceiling, car vinyl dashboards, aircraft overhead vents, flooring, and any forced air duct exits, there may be no metal for the magnetic to attach, an adhesive. In those scenarios, a backed magnet flexible gasket may be incorporated. This gasket may also serve as an elevated surface mount to avoid any existing protruding venting controls, on/off controls, directional knobs and/or elevator louvers and other similar elements.

In public settings like airline jets, office workspaces, a double-sided/+&−North and South Pole magnet application would apply. This would allow for a quick filter change out, while the original magnetic filters base would stay fixed adhered to the original factory constructed surface. In addition this removable top fascia is also printable for branding, advertisements, or any other forms of graphics. In addition, this system accommodates various types, and or benefits including interchangeable, disposable filters, such as a variety of scents.

Also 100% disposable non-reusable frames applications would be constructed from and hospital sanitation issues. The filters components are made from a combination of flexible and or ridged, single and or double-sided polypropylene, and or printable vinyl laminates, paper and plastic liners, and magnetic structures. The filters could effectively be made from a non-woven micro fiber, re-useable, synthetic, woven and/or washable fibers.

Yet another objective, many duct air vent have louvered fins behind the vents fascia plate. These areas may not produce an airtight seal. If additional air duct blockage is requited. A vent-blocking insert mat may be used instead of the filter pad (12) this will assist in blocking hot, cold, or natural outdoor from entering through ducts vents.

Figure 10:
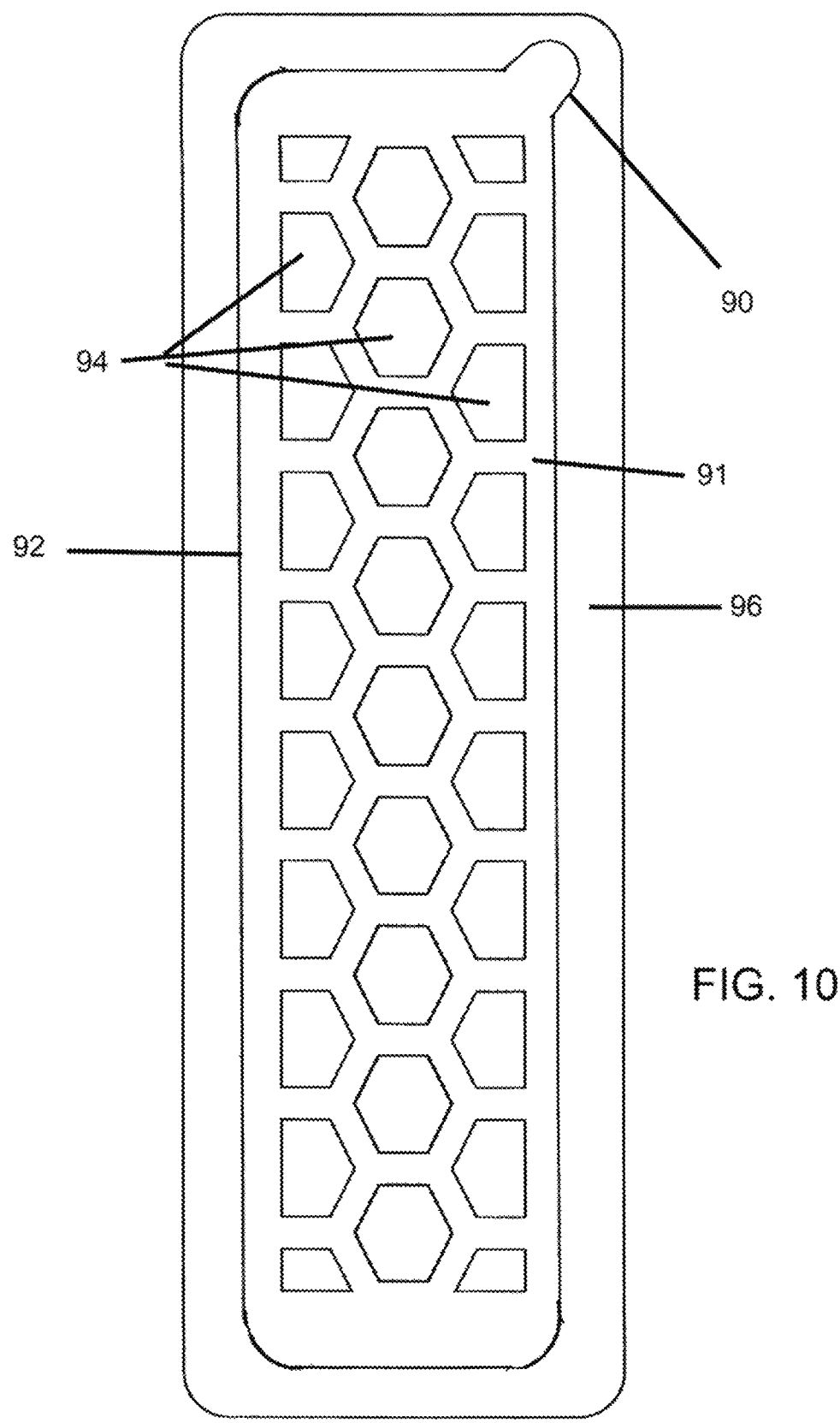
FIG. 10 A plan view of a version of a grille.

Now referring to FIG. 10 where a grille is shown to include, among other features, a tab 90, a sheet 91, an edge 92, apertures 94 and a margin 96. The grille is basically formed of a substrate visible in this view as the margin 96. The tab 90 can be pulled as part of the sheet 91, having an edge 92, that protects and adhesive layer underneath. When the adhesive layer is exposed a filter element can be adhered thereto. The grille can then be installed.

The apertures 94 are in a predetermined pattern, an example of which is in FIG. 10. Many other configurations are possible that would be equally effective. For example, patterns could be made of circles, squares, rectangles, diamonds, polygons or slits oriented in one or more directions could be used.

Figure 11:
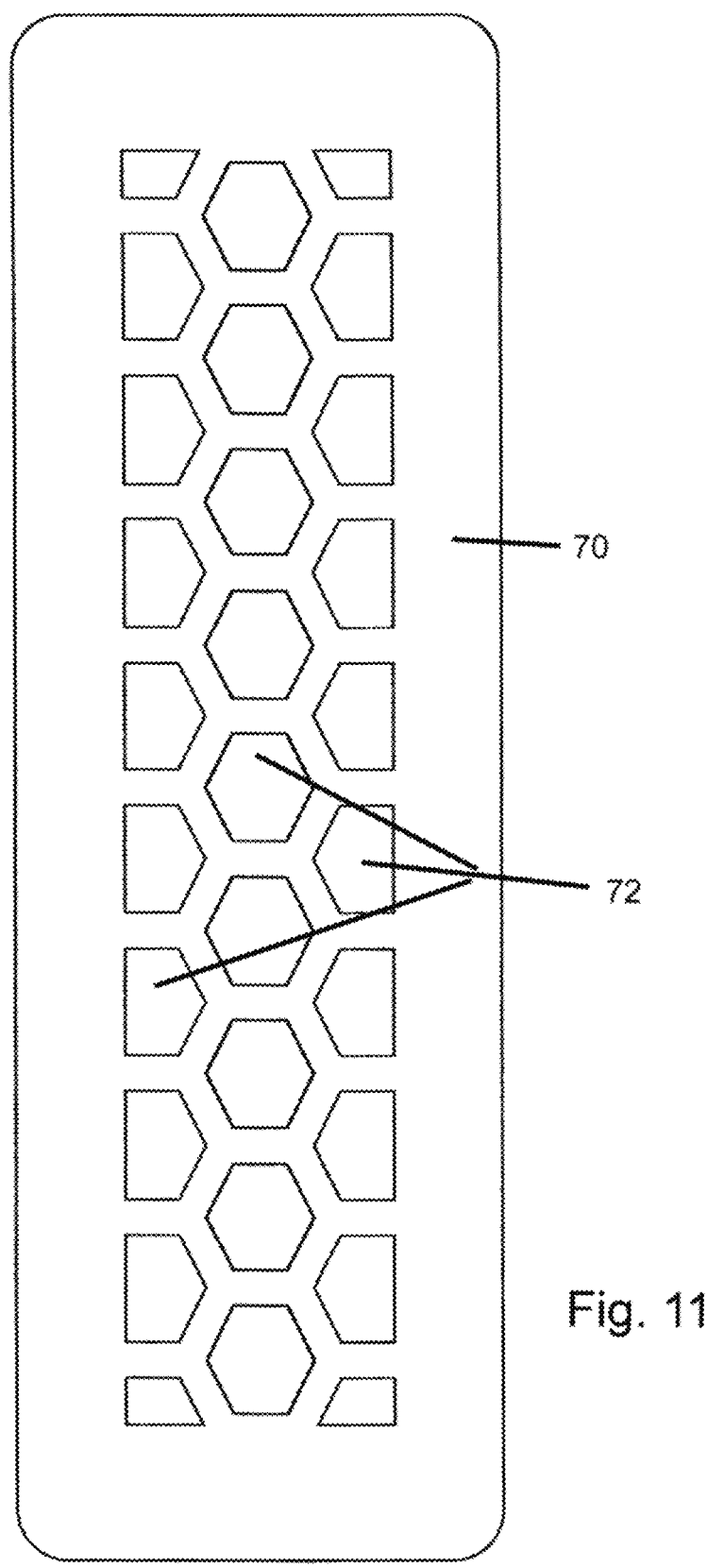
FIG. 11 A plan view of a version of a grille.

Referring to FIG. 11 where a grille is shown to have, among other elements, a substrate 70 with apertures 72. As in other variations of grilles, the air in the system flows through the apertures 72 while the substrate 70 provides structure upon which the filter elements or other features can be affixed or be supported.

Figure 12:
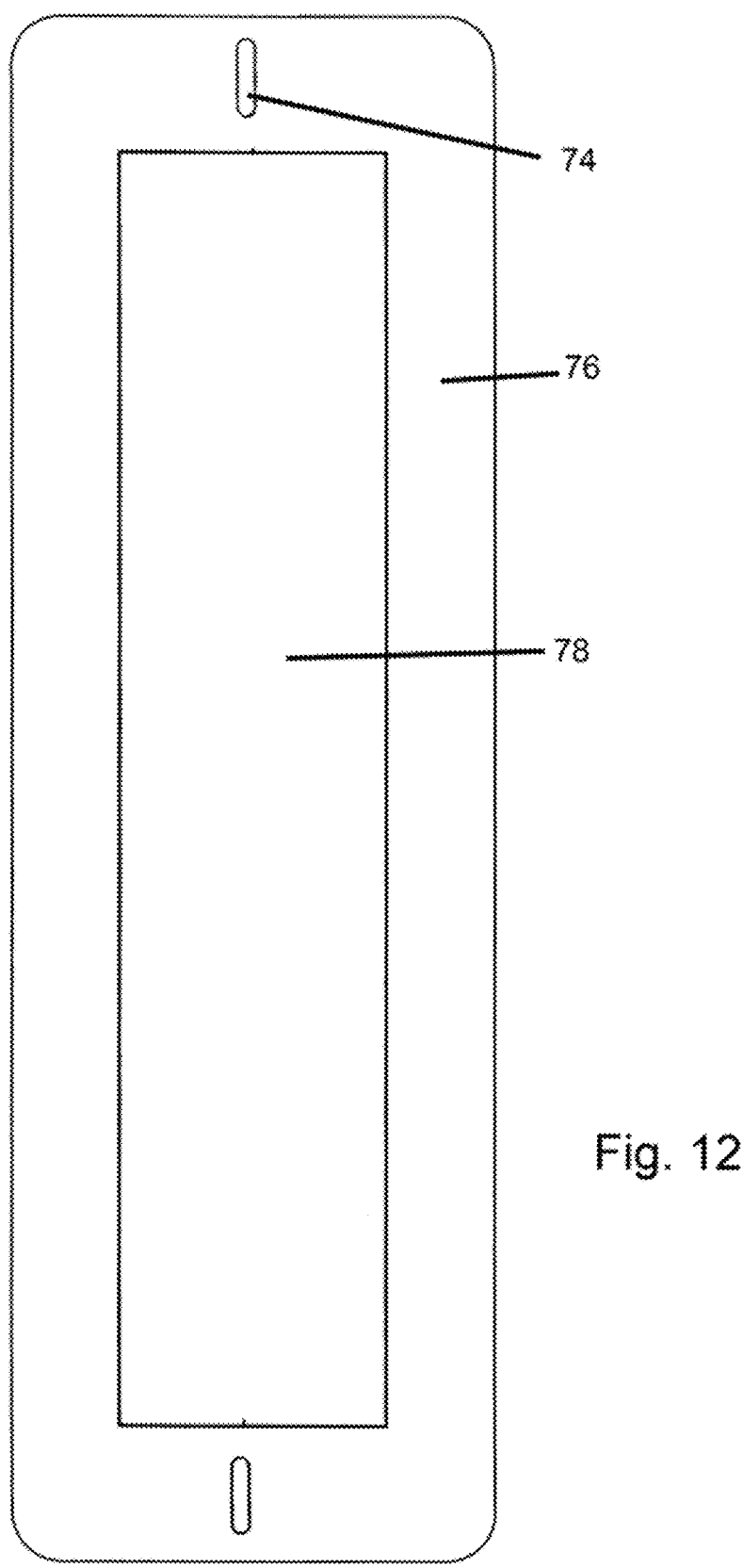
FIG. 12 A plan view of a version of a gasket.

FIG. 12 is an example of a gasket that can be used with a grille that includes a mounting hole 74, a margin 76 and an aperture 78. The margin 76 is generally a supple material suitable to act as a gasket or seal when used in conjunction with any of the varieties of grilles shown and described herein. The mounting holes 74 are optionally provided and if present may be located in several places along the margin 76 that match up with a particular application. The mounting holes 74 allow a fastener, such as a screw, to work with the gasket without producing damage and permitting re-use of the gasket.

Figure 13:
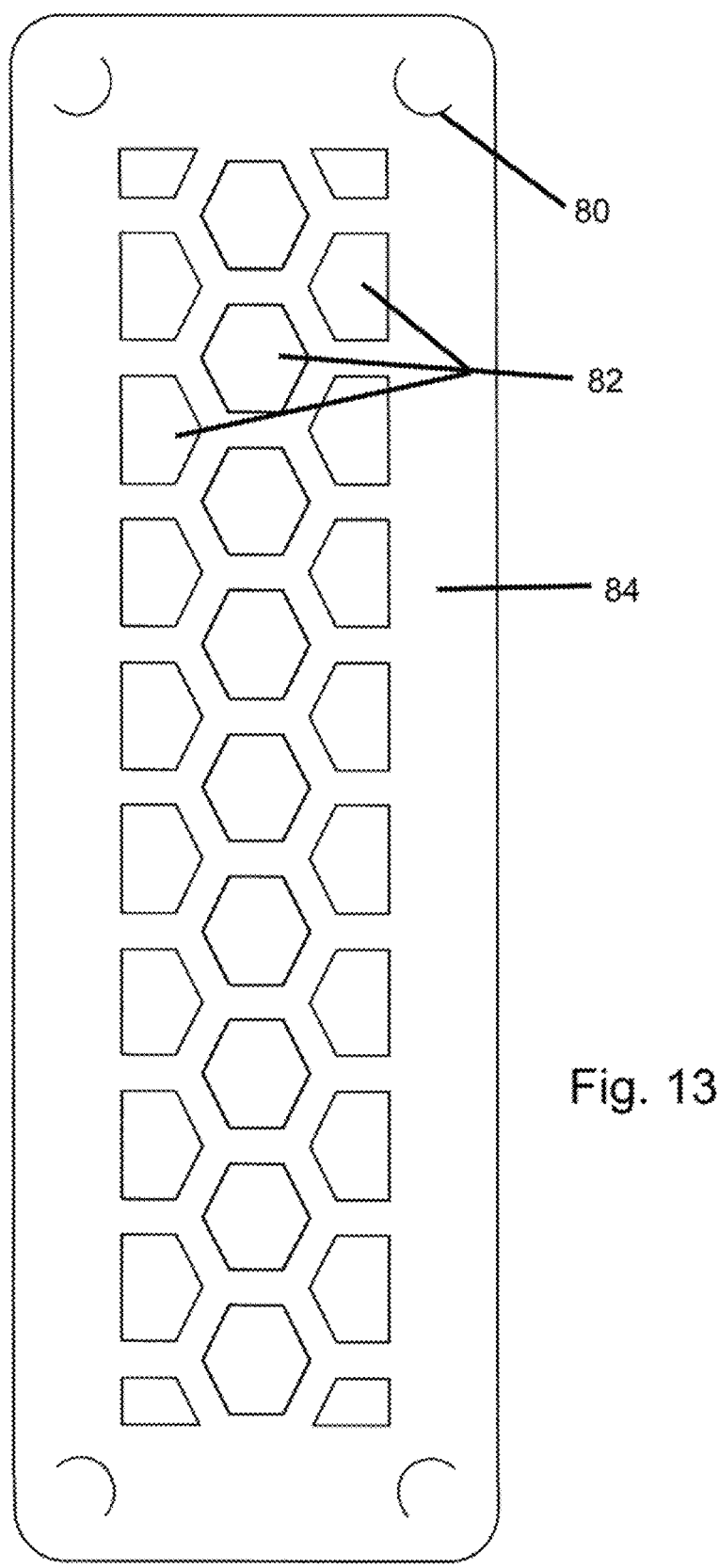
FIG. 13 A plan view of a version of a grille.

FIG. 13 is yet another version of a grille comprised of, among other features, tabs 80, apertures 82 and substrate 84. The tabs 80, in this version, are placed near the corners of the substrate 84. The tabs 80 can be used to aid in securing a filter media to the substrate 84. This can be particularly useful during installation and removal of the substrate 84 and any filter media being used.

Any of the examples of grilles shown in the figures and described above could be attached in a hinged fashion to the underlying ductwork or vent material onto which the grille is otherwise engaged. They could also be screwed, held by magnets, adhesive or any other available connecting means that remains within the spirit of the disclosure.

Any of the grilles could be fabricated of a stamped metal or plastic with the back portion being a laminated magnet, vinyl covered adhesive or flush mounted magnets. Other contemplated manufacturing processes include die cut, laser cut, digital knife cut, water jet cut, plasma cut, CNC cut or injection molding for any of the elements included in the grille, gaskets or filter elements.

The grille mat and related components could be constructed of aluminum or other metal, plastic or rubber. The gasket could also be made of rubber, cork, fabric material, foam or other suitable material known in the industry.

The devices disclosed herein can be used on both the supply and/or return side of HVAC systems. They could work equally well, with modification of materials remaining within the scope of the invention, to work on pool or spa filters in an underwater or surface mounted environment. Similarly, it could be used in other air moving applications not related to HVAC such as cooling fans on computers and other electrical equipment. It could also be applied to air exchange in kitchen and cooking applications where particulate matter and dissolved gasses in the air can be effectively filtered.

An important version of the HVAC filter can be fairly described as being comprised of a frame and a filter. The frame is dimensioned to completely cover a predetermined grate on an HVAC system. These can range from a few inches across to several feet or large in most applications. The frame has a margin that is in continuous and airtight contact with the grate. Essentially, the frame holds the filter against the grate. The grate is an existing part of the system. The frame includes a series of apertures inside the margin that allow airflow to pass through the frame and therefore also the filter. The material of the frame remaining around the apertures helps to support and hold flat the filter. The filter is dimensioned to match the dimensions of the frame so that they are typically about the same size but in some applications the filter is smaller than the frame. The airflow passing through the frame must pass through the filter necessarily because of the way that they are stacked on top of each other. Preferably the filter is electrostatically charged but it need not be in all applications. The filter is configured so that an airborne particulate is captured and held by the filter. The filter could be designed to capture 0.5 microns or less or could be made to capture anything above a preset point, for example 5 microns or larger. By adapting the size of the particles captures the filter's resistance or flow through rate can be adjusted as well as the size of material that is picked up by the filter.

In an option, the frame includes an adhesive layer on one side in contact with the filter to secure the filter to the frame. Or on both sides to further adhere the frame to the gasket or the gasket to the filter. Alternatively, these adhesion points could be magnetic or by other mechanical fastener.

Another option for an HVAC filter is that the filter includes activated carbon to filter out vapors dissolved the airflow, odors or other fine matter. In another option to the basic design of an HVAC filter a gasket is provided to ensure an airtight seal between the grate and the frame or the filter and the frame or the filter and the grate. The gasket could be made of a supple and flexible material suitable for making a tight seal.

In yet another option, on an HVAC filter the frame is attached to the grate by a mechanical means. For example, this could be done with screws, clips, magnets, snap on fit or friction fit or any combination thereof as may be suitable for a particular application.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

I claim:
1. An HVAC filter, the HVAC filter comprising:
   a frame mat, wherein the frame mat:
      is dimensioned to completely cover an opening of a grate on an HVAC system;
      has a margin that is in continuous and airtight contact with the grate; and
      includes a series of apertures inside the margin that allow an airflow to pass through the frame mat;
   a gasket, wherein the gasket is magnetically attached to the frame mat; and
   a filter, wherein the filter:
      includes a static charged material;
      covers the series of apertures; and
      is configured so that an airborne particulate is captured and held by the filter.

2. The HVAC filter of claim 1, wherein the filter includes one or more tabs, the one or more tabs configured to be inserted into the frame mat and secure the filter relative to the frame mat.

3. The HVAC filter of claim 1, wherein the filter includes activated carbon to filter out vapors dissolved the airflow.

4. The HVAC filter of claim 1, wherein the filter is secured between the gasket and the frame mat.

5. The HVAC filter of claim 1, wherein the gasket includes at least one of:
   rubber;
   cork;
   vinyl;
   fabric; or
   foam.

6. The HVAC filter of claim 1, wherein the filter includes at least one of:
   microfibers; or
   synthetic fibers.

7. The HVAC filter of claim 6, wherein the frame mat contains:
   flexible magnetic vinyl.

8. An HVAC filter, the HVAC filter comprising:
   a frame mat, wherein the frame mat:
      is dimensioned to completely cover an opening of a grate on an HVAC system;
      has a margin that is in continuous and airtight contact with the grate; and
      includes a series of apertures inside the margin that allow an airflow to pass through the frame mat;
   a filter, wherein the filter:
      includes a static charged material;
      covers the series of apertures; and
      is configured so that an airborne particulate is captured and held by the filter;
   a gasket attached to the frame mat, wherein:
      the gasket is magnetically attached to the frame mat;
      the filter is placed between the gasket and the frame mat; and
      the gasket has a margin that is in continuous and airtight contact with the grate; and
   attachment means for securing the gasket to the grate.

9. The HVAC filter of claim 8, wherein the filter includes a scent infused filter.

10. The HVAC filter of claim 8, wherein the filter is washable.

11. The HVAC filter of claim 8, wherein the attachment means includes an adhesive.

12. The HVAC filter of claim 11 further comprising:
   a sheet covering the adhesive, wherein the sheet is configured to protect the adhesive prior to use.

13. The HVAC system of claim 12, wherein the sheet includes a tab, the tab configured to allow a user to separate the sheet from the frame mat.

14. The HVAC filter of claim 8, wherein the frame mat includes at least one of:
   aluminum;
   metal;
   plastic;
   rubber;

PVC vinyl;
plastic;
cardboard; or
paper.

15. The HVAC filter of claim 8, wherein the filter frame mat includes an aperture configured to allow one or more portions of the grate to extend through the frame mat.

16. An HVAC system for circulating air throughout a structure, the HVAC system comprising:
a furnace;
a fan for moving air from the furnace out to the structure;
a first duct for determining the path of the air from the furnace to the structure;
a grate covering the opening of the duct within the structure;
an air return for returning air to the furnace;
an HVAC filter, the HVAC filter including:
  a frame mat, wherein the frame mat:
    is dimensioned to completely cover an opening of the grate on an HVAC system; and
    includes a series of apertures inside the margin that allow an airflow to pass through the frame mat;
  a filter, wherein the filter:
    includes a material that can be static charged;
    covers the series of apertures; and
    is configured so that an airborne particulate is captured and held by the filter;
  a gasket attached to the frame mat, wherein:
    the filter is placed between the gasket and the frame mat; and
    the gasket has a margin that is in continuous and airtight contact with the grate; and
  one or more magnets for securing the gasket to the grate to the grate.

17. The HVAC system of claim 16, wherein the shape of the series of apertures includes at least one of:
hexagons;
circles;
squares;
rectangles;
diamonds;
polygons; or
slits.

18. The HVAC system of claim 16, wherein the gasket creates an elevated surface:
allowing the filter to move freely with respect to the frame mat and the grate; and
preventing the filter from coming in contact with the grate on the air return.

19. The HVAC system of claim 16 wherein:
the air passing through the filter renews the static charge of the filter increasing the amount of particulate removed from the air and increasing the attraction between the filter and the frame mat.

* * * * *